US00PP27303P3

(12) United States Plant Patent
Helvick et al.

(10) Patent No.: US PP27,303 P3
(45) Date of Patent: Oct. 25, 2016

(54) ***LAGERSTROEMIA* PLANT NAMED 'PIILAG-VII'**

(50) Latin Name: ***Lagerstroemia* sp. hybrid**
Varietal Denomination: PIILAG-VII

(71) Applicant: Plant Introductions, Inc., Watkinsville, GA (US)

(72) Inventors: Rhonda Helvick, Madison, GA (US); Oren McBee, Bishop, GA (US); Mark Griffith, Watkinsville, GA (US); Jeff Beasley, Lavonia, GA (US); Michael A. Dirr, Bogart, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 103 days.

(21) Appl. No.: 14/121,501

(22) Filed: Sep. 12, 2014

(65) Prior Publication Data

US 2016/0081247 P1 Mar. 17, 2016

(51) Int. Cl.
*A01H 5/02* (2006.01)

(52) U.S. Cl.
USPC ..... Plt./252

(58) Field of Classification Search
USPC ..... Plt./252
See application file for complete search history.

*Primary Examiner* — June Hwu
(74) *Attorney, Agent, or Firm* — Lathrop & Gage LLP

(57) ABSTRACT

A new and distinct cultivar of *Lagerstroemia* plant named 'PIILAG-VII', characterized by its compact, upright, intermediate growth habit, reddish new growth, and lustrous dark green foliage in summer, red flowers where the petals cover the stamens, superior resistance to powdery mildew and *Cercospora* leaf spot, and increased cold hardiness.

2 Drawing Sheets

Genus and species of plant claimed: *Lagerstroemia* sp. hybrid.

Variety denomination: 'PIILAG-VII'.

BACKGROUND OF THE INVENTION

The present invention relates to a new and distinct cultivar of *Lagerstroemia* plant, botanically known as *Lagerstroemia* L. 'PIILAG-III'×*L. indica* 'Whit IV', commonly known as crapemyrtle, and hereinafter referred to by the cultivar name 'PIILAG-VII'. 'PIILAG-VII' is grown primarily as an ornamental for landscape use.

'PIILAG-VII' originated from controlled pollinations seed of *Lagerstroemia* L. 'PIILAG-III' (U.S. Plant Pat. No. 23,178)×*L. indica* 'WHIT IV' (U.S. Plant Pat. No. 11,342) growing in Watkinsville, Ga. The cultivar 'PIILAG-VII' originated in 2010 and was selected in a cultivated environment in Watkinsville, Ga. from the progeny of this cross-pollination by continued evaluation for growth habit, foliage, flower, and disease resistance characteristics.

Asexual reproduction of 'PIILAG-VII' by stem cuttings in Watkinsville, Ga. since 2011 has shown that all the unique features of this new *Lagerstroemia,* as herein described, are stable and reproduced true-to-type through successive generations of such asexual propagation.

SUMMARY OF THE INVENTION

Plants of the new cultivar 'PIILAG-VII' have not been observed under all possible environmental conditions. The phenotype may vary somewhat with changes in light, temperature, soil and rainfall without, however, any variance in genotype.

The following traits have been repeatedly observed and are determined to be unique characteristics of 'PIILAG-VII'. These characteristics in combination distinguish 'PIILAG-VII' as a new and distinct cultivar: 1. Compact and tight, dense, intermediate growth habit; 2. Red new growth; 3. Lustrous dark green foliage in summer; 4. Red flowers where stamens are covered by petals; 5. Superior resistance to powdery mildew and *Cercospora* leaf spot.

Plants of 'PIILAG-VII' differ from plants of the female parent 'PIILAG-III' (U.S. Plant Pat. No. 23,178) primarily in the color of new growth, the summer foliage, and the flowers. Plants of 'PIILAG-III' have red-purple new growth, dark green foliage in the summer, and red flowers that show their stamens, whereas plants of 'PIILAG-VII' have red new growth, lustrous dark green foliage, and the flowers cover the stamens.

Plants of 'PIILAG-VII' differ from plants of the parent, *L. indica* 'Whit IV' (U.S. Plant Pat. No. 11,342), primarily in habit, foliage color, flower color, and disease resistance. Plants of *L. indica* 'Whit IV' (U.S. Plant Pat. No. 11,342) have red-purple new growth, lighter green foliage color, red flowers, the stamens are visible, and poor resistance to *Cercospora* leaf spot, whereas plants of 'PIILAG-VII' have overall darker green foliage with red new growth, darker red flowers, and superior resistance to *Cercospora* leaf spot.

Plants of 'PIILAG-VII' can be compared to the cultivar 'Whit II' (U.S. Plant Pat. No. 10,296), but differ in growth habit, foliage color, flower appearance, overall size, and disease resistance. Plants of 'PIILAG-VII' have a compact and tight, upright, intermediate growth habit, new growth emerges red, the stamens on the flower are covered by the petals, and it has superior disease resistance to mildew and *Cercospora* leaf spot, whereas plants of 'Whit II' (U.S. Plant Pat. No. 10,296) have an overall larger, spreading growth habit, the leaves emerge crimson, the stamens are visible in the flowers, and it is highly susceptible to mildew and

*Cercospora* leaf spot. Plants of 'PIILAG-VII' are more cold hardy than plants of 'Whit II' (U.S. Plant Pat. No. 10,296).

BRIEF DESCRIPTION OF THE DRAWINGS

The accompanying color photographs illustrate the flower and foliage characteristics and the overall appearance of 'PIILAG-VII', showing the colors as true as it is reasonably possible to obtain in color reproductions of this type. Colors in the photographs may differ slightly from the color values cited in the detailed botanical description which accurately describe the colors of the new *Lagerstroemia*.

DETAILED DESCRIPTION

Figure 1:
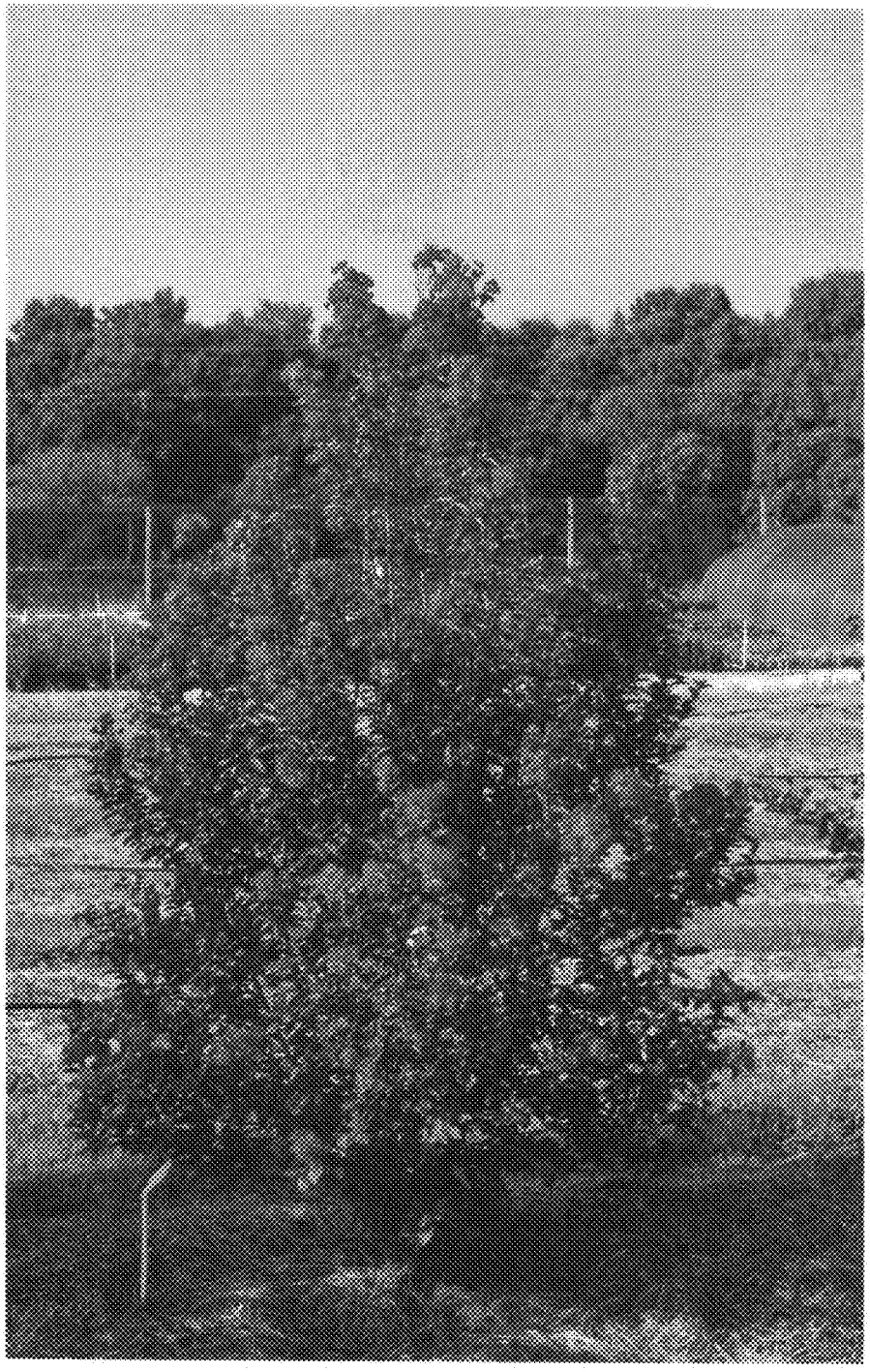
FIG. 1 illustrates the overall appearance of an established three-year-old plant of 'PIILAG-VII' planted in the ground.
Figure 2:
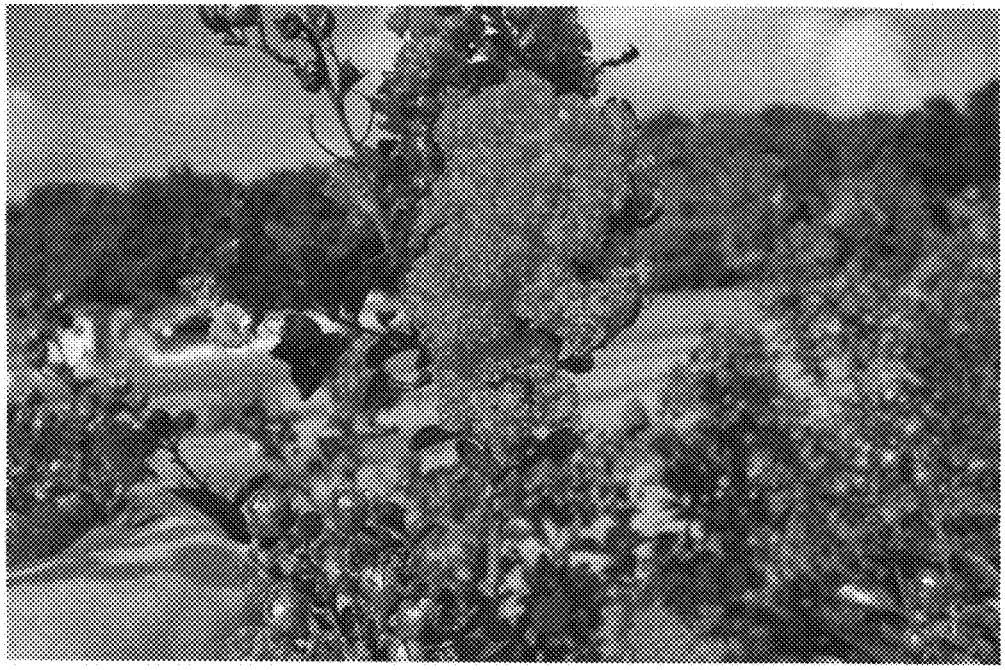
FIG. 2 illustrates a close-up view of the flower of a three-year-old 'PIILAG-VII' plant.

In the following description, color references are made to The Royal Horticultural Society Colour Chart, 2007 Edition, except where general terms of ordinary dictionary significance are used. Plants used for the description were approximately two-years-old and were grown in 11.8 L containers under outdoor conditions in Watkinsville, Ga. Colors are described using The Royal Horticultural Society Colour Chart (R.H.S.).

Botanical classification: *Lagerstroemia* L., cultivar 'PIILAG-VII'.

Parentage:

- *Female, or seed, parent.*—*Lagerstroemia* 'PIILAG-III' (U.S. Plant Pat. No. 23,178).
- *Male, or pollen Parent.*—*Lagerstroemia indica* 'WHIT IV' (U.S. Plant Pat. No. 11,342) (controlled-pollinated).

Propagation: Terminal cuttings.

- *Time to initiate roots, summer.*—About 21 days at 32° C.

Plant description:

- *Flowering shrub.*—Compact, upright, intermediate growth habit. Freely branching; lateral branches abundant without pruning, resulting in fine-textured, dense habit.
- *Root description.*—Numerous, fine, fibrous and well-branched.
- *Plant size.*—The original plant, now about four-years-old in the ground, is about 183 cm high from the soil level to the top of the inflorescences and about 94 cm wide. First year stems have a diameter of about 2.5 mm. First year stems have a length of 30 cm to 46 cm. Shape: squarish. Second year and older stems have a diameter of about 5 mm or more. Second year stems have a length of 61 cm to 91 cm. Shape: round.
- *Trunk diameter.*—3 cm at the soil line. Color: N199D.
- *Internode length.*—About 1.5 cm.
- *Strength.*—Flexible when young, easily broken once mature.
- *First year stem color* (*young*).—53A. Color (woody): 200D.
- *Second year and older stem color.*—N199D.
- *Bark.*—Minor exfoliation in strips beginning on second or third year stems.
- *Exfoliation color.*—199B. Exfoliation approximately 7 cm in length and 1 cm in width.

Vegetative buds: Sub-opposite to alternate in arrangement, imbricate, conical, with no pubescence.

- *Color.*—53A.
- *Size.*—About 2.5 mm in length and 1 mm in width.

Foliage description:

- *Arrangement.*—Sub-opposite to alternate, simple.
- *Length.*—About 4 cm.
- *Width.*—About 2.5 cm.
- *Shape.*—Elliptical to ovate.
- *Apex.*—Acuminate.
- *Base.*—Cuneate.
- *Margin.*—Entire.
- *Texture* (*upper and lower surfaces*).—Glabrous and glossy.
- *Venation pattern.*—Pinnate.
- *Venation color of emerging foliage* (*upper and lower surfaces*).—53A.
- *Venation color of fully expanded foliage* (*upper and lower surfaces*).—53C.
- *Color in developing foliage* (*upper and lower surfaces*).—53A.
- *Color in fully expanded foliage* (*upper surface*).—139A.
- *Color in fully expanded foliage* (*lower surface*).—146A.
- *Petiole length.*—About 2 mm.
- *Petiole diameter.*—About 1 mm.
- *Petiole color* (*upper and lower surfaces*).—53A.
- *Pubescence.*—None.
- *Fall color.*—Can be 180B, 23B or any combination of these colors. The leaves in the fall are anywhere from yellow-orange to a grey-red.

Flower description: Flowers are produced from about June to September in Watkinsville, Ga. An inflorescence is showy for about two weeks, and individual flowers last about one day and are self-cleaning. Flowers are lightly fragrant.

- *Inflorescence type.*—Panicle. Panicle contains between 30-50 flower buds and flowers. Inflorescence length: about 11.5 cm. Inflorescence width: about 10 cm.
- *Peduncle.*—About 8.6 cm in length, about 2 mm in diameter, color is 53A, and no pubescence.
- *Individual flowers.*—About 2 cm in height and 3 cm in diameter.
- *Flower buds.*—Length: about 1 cm; Diameter: about 1 cm; Color: 46B. Unopened flower buds are globose with six distinct lines of dehiscence where they split to reveal the petals.
- *Sepals.*—Arrangement/quantity: single whorl of six basal fused sepals separated at the apex. Length about 9 mm. Width: about 4 mm. Shape: elliptical. Apex: acute. Margin: entire. Texture, upper and lower surfaces: smooth, glabrous. Color when opening, upper surface: 179A. When opening lower surface: 179B. Fully opened, upper surface: 179A. Fully opened, lower surface: 179B.
- *Pedicels.*—About 8 mm in length, 1 mm in diameter, 179B in color, and no pubescence.
- *Calyx.*—About 8 mm in length, about 1 cm in diameter, 179B in color on both surfaces, and no pubescence.

Petals:

- *Arrangement/appearance.*—Usually 6 or 7 per flower.
- *Petal length.*—About 1.5 cm.
- *Petal width.*—About 1.3 cm.
- *Petal shape.*—Fan-shaped, fan-shape covers the stamens. Petal apex: ruffled, rounded. Petal base: sagittate. Petal margin: undulate. Petal texture (upper and lower surfaces): glabrous.

*Petal color.*—Upper and lower surfaces are 46A.

Stamens:

*Quantity/arrangement.*—About 25 to 30 short stamens clustered in the center, about 1.5 cm long, filament color is 35C, and anther color is 7A. The short stamens are surrounded by 6 longer stamens, about 2 cm long, filament color is 35C, and anther color is 7A. The stamens are not pubescent. Pollen: produced in moderate quantities and is 7A in color on the short and long stamens.

Pistils:

*Quantity.*—One superior pistil per flower.

*Pubescence.*—None.

*Pistil length.*—About 1.9 cm in length.

*Stigma shape.*—Round, about 1 mm in diameter.

*Stigma color.*—N172A.

*Style color.*—46A and about 1.5 cm in length.

*Ovary color.*—2B and about 2.5 mm in diameter.

Fruit:

*Type/appearance.*—Six-valved, dehiscent, broad ellipsoidal capsule.

*Length.*—About 8 mm.

*Diameter.*—About 8 mm.

*Immature color.*—144B.

*Mature color.*—200C. Each capsule contains about 30 seeds that are about 5 mm long, 3 mm wide, and 200C in color.

Plant hardiness:

*Plant hardiness.*—USDA Hardiness Zone Map (2012): Zone 6 to 9.

Disease/pest resistance: Plants of the claimed *Lagerstroemia* variety grown in field and container trials have exhibited superior resistance to powdery mildew and *Cercospora* leaf spot.

We claim:

1. A new and distinct *Lagerstroemia* plant named 'PIILAG-VII', as illustrated and described herein.

* * * * *